US00PP09425P

United States Patent [19]

Frazer

[11] Patent Number: Plant 9,425

[45] Date of Patent: Jan. 9, 1996

[54] DIEFFENBACHIA PLANT NAMED TROPIC FOREST

[75] Inventor: Edwin J. Frazer, Kenmore, Australia

[73] Assignee: Twyford International Inc., Sebring, Fla.

[21] Appl. No.: 374,858

[22] Filed: Jan. 19, 1995

[51] Int. Cl.[6] ..... A01H 5/00

[52] U.S. Cl. ..... Plt./88.2

[58] Field of Search ..... Plt./88.2

*Primary Examiner*—James R. Feyrer
*Attorney, Agent, or Firm*—Foley & Lardner

[57] ABSTRACT

A Dieffenbachia plant named Tropic Forest particularly characterized by its very large ovate leaves marked with yellow green, and its large upright growth habit.

2 Drawing Sheets

The present invention comprises a new and distinct cultivar of Dieffenbachia, botanically known as *Dieffenbachia hybrida*, and referred to by the cultivar name Tropic Forest.

The new cultivar is a product of a planned breeding program carried out by the inventor Edwin J. Frazer in Brisbane, Australia. The new cultivar is a product of a cross made between the following:

Pollen parent: An unidentified species designed Birdsey No. 4.

Seed parent: An unidentified species designated Marie Selby 79-92.

The cultivar was discovered from the progeny of the stated cross by Edwin J. Frazer. Asexual propagation by tissue culture by the inventor in Brisbane, Australia increased the number of plants for evaluation and has demonstrated the stability of the combination of characteristics of Tropic Forest from generation to generation.

The following observations, measurements and values describe plants grown in Apopka, Fla. under greenhouse conditions which closely approximate those generally used in horticultural practice.

The following traits have been repeatedly observed to be characteristics which in combination particularly distinguished Tropic Forest as a unique new cultivar.

1. The growth habit of Tropic Forest is tall and upright with few branches.

2. The leaves of mature plants are medium green marked with large yellow-green spots.

3. The leaves of Tropic Forest are very large, and often curved downward at the tip.

All color references are measured against The Royal Horticultural Society Colour Chart. Colors are approximate as colors depends on horticultural practices such as light level and fertilization rate, among others, without, however any variance in genotype.

In the accompanying photographic drawings, the photograph on Sheet 1 comprises a top perspective view of a plant of Tropic Forest grown in a 21 cm pot, approximately 40 weeks after planting a 12-week-old liner obtained by tissue culture and grown under appropriate growing conditions.

The photograph on sheet 2 illustrates the leaf color and pattern in much greater detail.

Colors are as accurate as possible with color illustrations of this type.

Origin: Sterile seedling selected from the progeny of a cross between Birdsey No. 4, the pollen parent, and Marie Selby 79-92, the seed parent.

Classification: *Dieffenbachia hybrids*, cv., Tropic Forest.

Propagation: Asexual propagation either by tissue culture of division.

Plant: In a 21 cm pot for a plant grown from a 12 week old liner after 40 weeks under appropriate growing conditions, Tropic Forest has a height of approximatley 38 cm to 40 cm from the soil surface to the junction of the petioles of the last two (2) unrolled leaves, and a width of approximately 90 cm to 95 cm.

Stem:

*Growth pattern.*—The stem is erect in growth and is approximately 4.4 cm to 4.9 cm in diameter five (5) cm above the soil surface. Internode distance is approximately 1.9 cm to 2.4 cm three (3) cm above the soil.

*Color.*—The stem is mottled with blotches of dark green (greener than, but closest to 139A) and light greenish white.

Petiole: The following information is based on the 4th expanding leaf from the apex.

*Growth pattern.*—The petiole has fleshy edges, referred to as wings, extending from the midrib. The wings are approximately 11 mm to 18 mm wide one-half (½) the distance from the petiole base to the wing apex, and extend from the base of the petiole to within approximately 3.4 cm to 4.2 cm of the base of the leaf. The apex of the wings is unevenly emarginate. The petiole follows the stem axis but diverges from the axis approximately 10.3 cm from the leaf base, forming a horizontal distance from the edge of the stem to the leaf base of approximately 3.5 cm to 4 cm.

*Dimensions.*—The petiole is straight from its base to the tip of the wings, and curved from the tip of the wings to the base of the leaf. The petiole is approximately 11 mm in diameter one-half (½) the distance between the top of the wing and approximately 23.2 cm to 25 cm in length from its base to the base of the leaf.

*Color.*—The petiole wings are darker and greener than, but closest to 139A. The midrib of the petiole is darker and greener than, but closest to 139A, streaked with 145C near the base. The surface texture of the petiole and petiole wings is dull to matte.

Leaf:

*Growth pattern.*—The leaf is ovate with a cuspidate apex and an obtuse base. The margin is entire. The leaf is asymmetric with the side of the leaf unrolling first having less surface area than the side unrolling last. The leaf is oriented parallel to the stem axis at the time of full unrolling, changing to approximately 40 degrees from the stem axis as more leaves unroll above it. The midrib is straight over the length of the leaf. However, as the leaf ages, the distal third (⅓) of the midrib and leaf blade curves downward. The leaf blade is flat from the midrib to the margin, drooping slightly near the edge.

*Dimensions.*—For the pot size and growing time indicated, the largest leaf is approximately 54 cm to 56 cm long and approximately 24.4 cm to 26 cm wide. An average-sized leaf is approximately 42 cm to 44.6 cm long and approximately 18.5 cm to 19.3 cm wide. The leaf blade is moderately thick with a wavy puckered appearance, particularly along the midrib. The leaf surface is matte to satin in sheen.

*Midrib.*—The midrib is thick and prominent.

*Primary veins.*—The primary veins are sunken into the upper surface and protrude from the underside. The primary veins are the same color as the tissue surrounding them.

*Pattern.*—The leaf color pattern of Tropic Forest changes notably as the plant matures. Mature leaves are prominently marked with large yellow-green blotches on a medium green background. The color and pattern is visible from both sides of the leaf. The immature leaf pattern is similar. However, in addition to the above markings, the immature leaf is also variably overlaid with a mosaic of greenish white and dark green speckles and blotches. The mosaic of greenish white and dark green disappears as the plant matures, and is visible only on the upper surface.

*Color.*—Mature leaf pattern (upper surface): Darker and greener than, but closest to 139A, with large blotches of 144A. Midrib: Darker than, but closest to 137A. Newly emerged mature leaf: Greener than, but closest to 137A, with large blotches of 150C. Midrib: 146C. Mature leaf pattern (lower surface): 137B, with blotches lighter than but closest to 146D. Midrib: 146C–D. Newly emerged mature leaf: 137C with blotches of 145C. Midrib: 146D. Immature leaf pattern (upper surface): Darker and greener than, but closest to 139A with large blotches of 144A. Mosaic Pattern: 145A, with speckles and blotches darker and greener than, but closest to 139A. Midrib: 146C speckled with 145A. Newly emerged immature leaf: Greener than, but closest to 137A, with large blotches of 150C. Mosaic Pattern: 145A with speckles and blotches darker and greener than, but closest to 139A. Midrib: 146C. Immature leaf pattern (lower surface): 137B, with blotches lighter than, but closest to 146D. Midrib: 146C–D. Newly emerged immature leaf: 137C with blotches of 145C. Midrib: 146D. Axillary breaks: There are approximately 1 to 3 axillary breaks with at least one leaf expanded. Leaves will show color by the second leaf and pattern by the third leaf. The mature leaf color pattern aplpears by the fifth or sixth leaf.

*Inflorescence.*—Typical of Dieffenbachia and does not have commercial significance.

Roots: Thick white roots with fine laterals.

General observations: Tropic Forest has very large ovate medium green leaves marked with yellow-green blotches. The plant habit is large and upright with few branches. These combined characteristics make Tropic Forest a unique new cultivar.

It is claimed:

1. A new and distinct cultivar of Dieffenbachia plant named Tropic Forest, as illustrated and described.

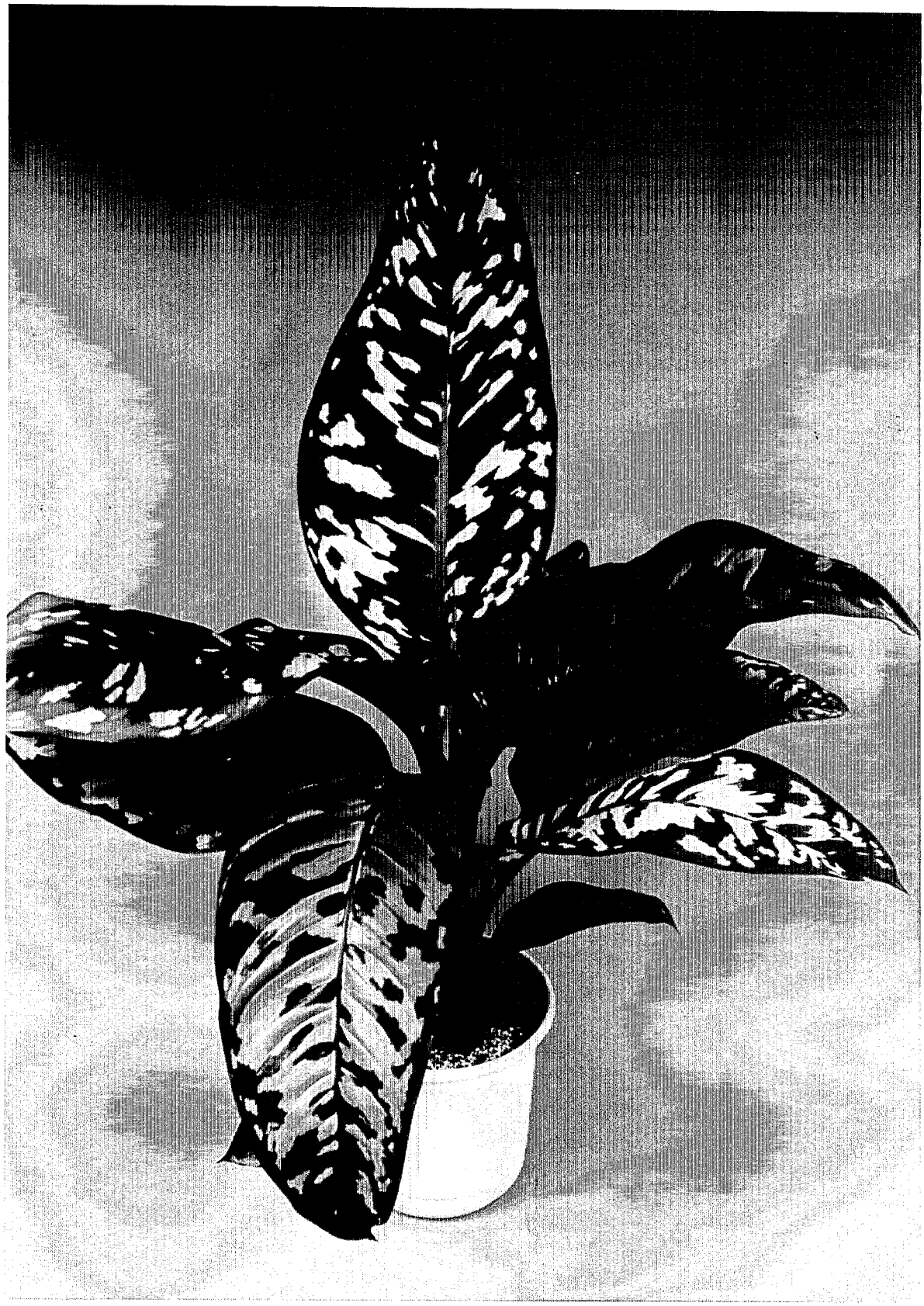

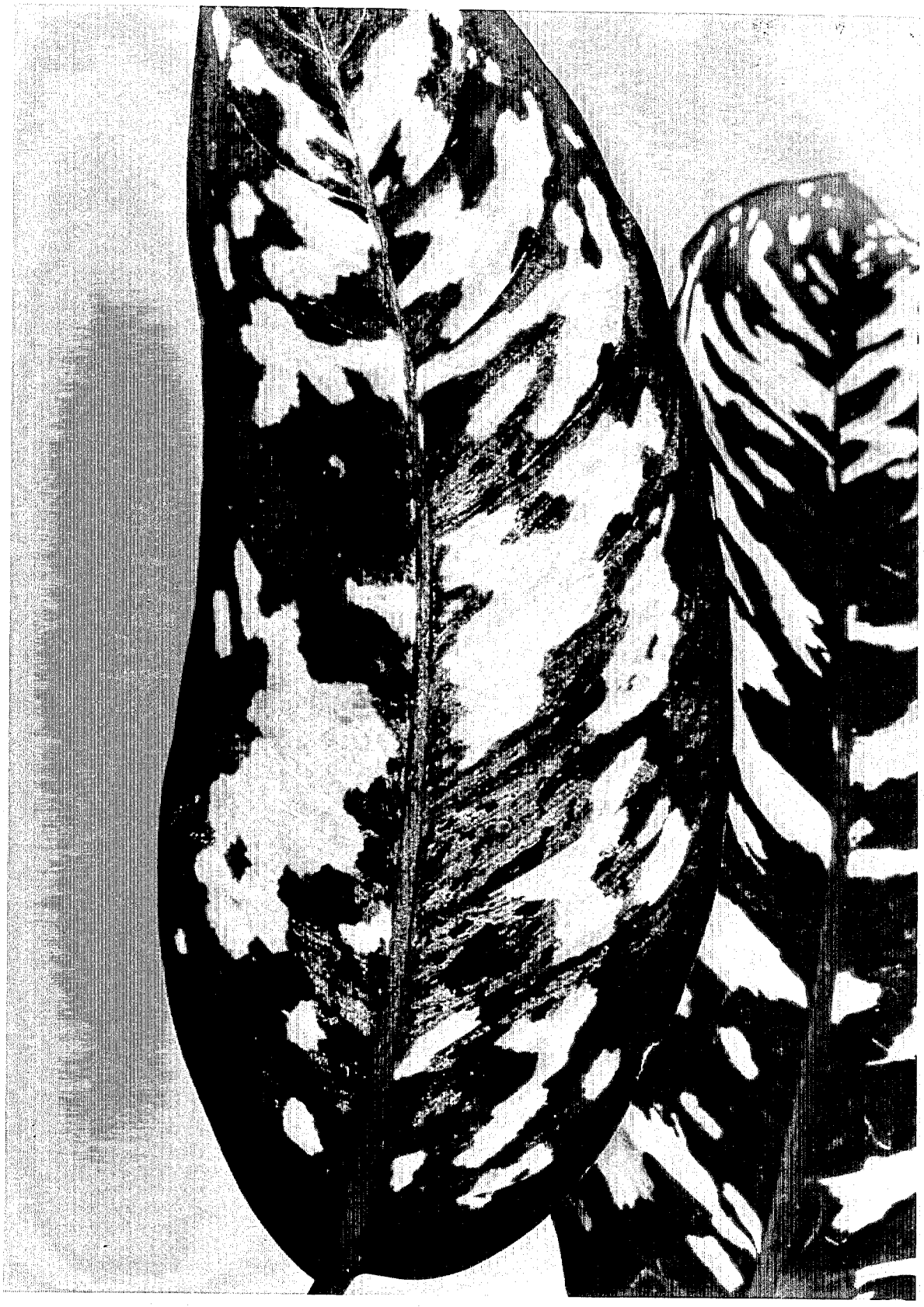

* * * * *